US011643626B2

(12) United States Patent
Meyer et al.

(10) Patent No.: US 11,643,626 B2
(45) Date of Patent: May 9, 2023

(54) WELL PLATE

(71) Applicant: Georg-August-Universitaet Goettingen Stiftung Oeffentlichen Rechts, Universitaetsmedizin, Goettingen (DE)

(72) Inventors: Tim Meyer, Goettingen (DE); Wolfram-Hubertus Zimmermann, Goettingen (DE); Malte Tiburcy, Goettingen (DE)

(73) Assignee: GEORG-AUGUST-UNIVERSITAET GOETTINGEN STIFTUNG OEFFENTLICHEN RECHTS, UNIVERSITAETSMEDIZIN, Goettingen (DE)

( * ) Notice: Subject to any disclaimer, the term of this patent is extended or adjusted under 35 U.S.C. 154(b) by 1121 days.

(21) Appl. No.: 16/207,392

(22) Filed: Dec. 3, 2018

(65) Prior Publication Data
US 2019/0106663 A1 Apr. 11, 2019

Related U.S. Application Data

(63) Continuation of application No. PCT/EP2017/062755, filed on May 26, 2017.

(30) Foreign Application Priority Data

Jun. 3, 2016 (DE) .................. DE10 2016 110 328

(51) Int. Cl.
*C12M 1/32* (2006.01)
*C12M 3/00* (2006.01)
(Continued)

(52) U.S. Cl.
CPC ............ *C12M 23/12* (2013.01); *C12M 21/08* (2013.01); *C12M 23/10* (2013.01); *C12M 23/48* (2013.01);
(Continued)

(58) Field of Classification Search
None
See application file for complete search history.

(56) References Cited

U.S. PATENT DOCUMENTS

| 7,618,452 B2 | 11/2009 | Eschenhagen |
| 10,034,738 B2 | 7/2018 | Thavandiran |
| 2009/0068701 A1 | 3/2009 | Elson et al. |

FOREIGN PATENT DOCUMENTS

| DE | 100 03 521 A1 | 8/2001 |
| JP | 2016-504022 | 2/2016 |

(Continued)

OTHER PUBLICATIONS

A. Hansen et al.: Development of a drug screening platform based on engineered heart tissue, Circ Res 107: 35-44, 2010.
(Continued)

*Primary Examiner* — Erin M. Bowers
(74) *Attorney, Agent, or Firm* — Thomas | Horstemeyer, LLP

(57) ABSTRACT

A well plate comprises a plate main body and at least one cavity in an upper side of the plate main body. An upwardly open annular channel is formed in the at least one cavity, the annular channel being delimited at an inner circumference thereof by a closed circumferential wall. A horizontal outer circumference of the circumferential wall decreases from bottom to top up to an upper edge of the circumferential wall. Within the horizontal circumference of the circumferential wall, at its upper edge, at least two retaining elements connect upwardly to the upper edge of the circumferential wall. The at least two retaining elements are at a free horizontal distance to one another, and at least one of the at least two retaining elements is elastically supported at the plate main body in horizontal direction.

30 Claims, 4 Drawing Sheets

(51) Int. Cl.
  *C12M 1/42* (2006.01)
  *C12M 1/34* (2006.01)
  *C12M 1/12* (2006.01)
  *C12M 1/22* (2006.01)
  *C12N 13/00* (2006.01)

(52) U.S. Cl.
  CPC ............ *C12M 25/14* (2013.01); *C12M 35/02* (2013.01); *C12M 41/46* (2013.01); *C12N 13/00* (2013.01)

(56) References Cited

FOREIGN PATENT DOCUMENTS

| WO | 2007/054286 A1 | 5/2007 |
| WO | 2014/154704 A1 | 10/2014 |
| WO | 2015/061907 A1 | 5/2015 |

OTHER PUBLICATIONS

W.-H. Zimmermann et al.: Tissue Engineering of a Differentiated Cardiac Muscle, Construct. Circ. Res. 90:223-230, 2002.

WELL PLATE

CROSS REFERENCE TO RELATED APPLICATIONS

The present application is continuation to international patent application PCT/EP2017/062755 filed on May 26, 2017, entitled "Perforated Plate" and claiming priority to German patent application DE 10 2016 110 328.4 filed on Jun. 3, 2016, entitled "Lochplatte", to which German patent DE 10 2016 110 328 B3 has been granted on Sep. 7, 2017.

FIELD OF THE INVENTION

The invention relates to a well plate comprising a plate main body and at least one cavity in an upper side of the plate main body, wherein an upwardly open annular channel is formed in the at least one cavity, the annular channel, at an inner circumference thereof, being delimited by a circumferential wall.

Particularly, the invention relates to a well plate comprising a plurality of such cavities for producing and investigating rings of artificial tissue produced by so-called tissue engineering, for example myocardial muscle and skeletal muscle tissue and connective tissue, wherein the term ring is to be understood such that the respective tissue forms a closed loop but not such that this loop has to have a particular geometric shape or even to be circular.

Further, the invention relates to a method of use of such a well plate particularly in the course of the manufacture and investigation of rings of artificial myocardial muscle and skeletal muscle tissue.

BACKGROUND OF THE INVENTION

A culture disc comprising a cavity in which an annular channel is formed by inserting a central cylinder of hydrophobic material, the annular channel being delimited at an inner circumference thereof by the outer circumference of the cylinder, is known from DE 100 03 521 A1, corresponding to U.S. Pat. No. 7,618,452 B2. When a special suspension of a hydrogel and of myocardial cells is placed in the annular channel, an artificial myocardial muscle tissue is made in a shape of a ring enclosing the cylinder.

According to WO 2007/054286 A1, this ring may be removed from the cylinder and arranged on two retaining fingers, so-called stretchers, which are parallel with regard to each other and which are elastically supported at each other in the direction of their distance. On these stretchers, the ring of artificial myocardial muscle tissue matures in culture medium and automatically starts with periodic contractions at a typical heart rate.

In the known culture disc with the central vertically oriented cylinder, artificial skeletal muscle tissue may also be made by filling-in a special suspension of hydrogel and skeletal muscle cells. For maturing, the ring of artificial skeletal muscle tissue made in this way has also to be arranged in culture medium on stretchers. It does, however, not automatically display rhythmical contractions but has to be electrically excited for this purpose.

In the known culture disc with the central vertically oriented cylinder, artificial connective tissue may also be made by filling-in a special suspension of hydrogel and connective tissue cells. For maturing, the ring of artificial connective tissue made in this way has also to be arranged in culture medium on stretchers. It is not capable of rhythmic contractions but tonically pulls the stretchers together depending on the tissue tension.

Relocating the rings of artificial tissue from the central cylinder in the cavity of the culture disc is laborious and may not be automated without further measures. Thus, extensive investigations using rings of artificial tissue are not possible in a reasonable way.

A device for measuring the contraction properties of artificial myocardial muscle tissue is known from WO 2014/154704 A1. For the measurement, a suspension of a hydrogel and of myocardial muscle cells in water is placed in a culture disc. Lower ends of two essentially vertically oriented retaining fingers which are bent outwardly away from each other are immersed into the suspension. Under suitable conditions, the polymerizing hydrogel with embedded myocardial muscle cells attaches thereto out of the suspension such that it forms a bone shaped construct connecting the free ends of the retaining fingers. By means of the device, the construct is removed out of the cavity of the well plate and transferred into a culture medium in a cavity in another well plate. Contraction movements of this construct are monitored by means of a piezoelectric transducer via which the retaining fingers are supported at a base of the device. The device and its use are complex and accident-sensitive and thus not reasonably applicable for extensive investigations of a plurality of tissue constructs under different boundary conditions.

A device without piezoelectric transducer, which is similar to the device known from WO 2014/154704 A1 is known from A. Hansen et al.: Development of a screening platform based on engineered heart tissue, Circ Res 107: 35-44, 2010. Here, the retaining fingers are elastically supported at the base of the device, and contraction movements of the bone shaped construct connecting the holding fingers are registered by optically monitoring the resulting movements of the holding fingers by means of a camera. Particularly, the change of the distance of opposing vertical surfaces of the holding fingers are monitored. Prior to that, a plurality of constructs, each between the lower ends of a pair of retaining fingers, are simultaneously made in a plurality of wells of a well plate whose horizontal cross-sections are adapted to a desired shape of the constructs, and then transferred with the device into wells of a further well plate filled with culture medium.

A well plate comprising a plurality of wells each provided for producing a string of artificial muscle tissue is known from WO 2015/061907 A1. In each cavity of the well plate, frame work elements are arranged which are fixed to a plate main body of the well plate and which are provided to be embedded in the respective string. In case of contractions of the string, the frame work elements embedded therein move. The contraction of the string may be excited by means of a pair of electrodes which are arranged on the frame work elements. In the known well plate, the effects of different substances like therapeutics and toxins on the contraction of the string shall be investigated. In the known well plate, the embedded frame work structures affect the properties of the tissue string.

There still is a need of a well plate and a method of its use by which, without much effort, extensive investigations may be conducted simultaneously and automatically at a high number of rings of artificial myocardial muscle or skeletal muscle tissue and of other tissue types.

SUMMARY OF THE INVENTION

The present invention relates to a well plate comprising a plate main body, at least one cavity in an upper side of the plate main body, an upwardly open annular channel being formed in the at least one cavity, a closed circumferential wall delimiting the annular channel at an inner circumference thereof, wherein a horizontal outer circumference of the circumferential wall decreases from bottom to top up to an upper edge of the circumferential wall, and at least two retaining elements connecting upwardly to the upper edge of the circumferential wall, within the horizontal circumference of the circumferential wall at its upper edge. The at least two retaining elements are at a free horizontal distance (28) to one another, and at least one of the at least two retaining elements is elastically supported at the plate main body in horizontal direction.

Further, the present invention relates to a method of use of such a well plate in which each of the at least two retaining elements is a part of one of at least two retaining fingers extending in vertical direction, the method of use comprising the steps of placing a suspension of connective tissue cells and further cells into the annular channel, filling the cavity with a culture medium up to above the at least two retaining elements, and monitoring movements of at least one free upper end of at least one of the at least two retaining fingers with a camera.

Other features and advantages of the present invention will become apparent to one with skill in the art upon examination of the following drawings and the detailed description. It is intended that all such additional features and advantages be included herein within the scope of the present invention, as defined by the claims.

SHORT DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESCRIPTION

Figure 1:
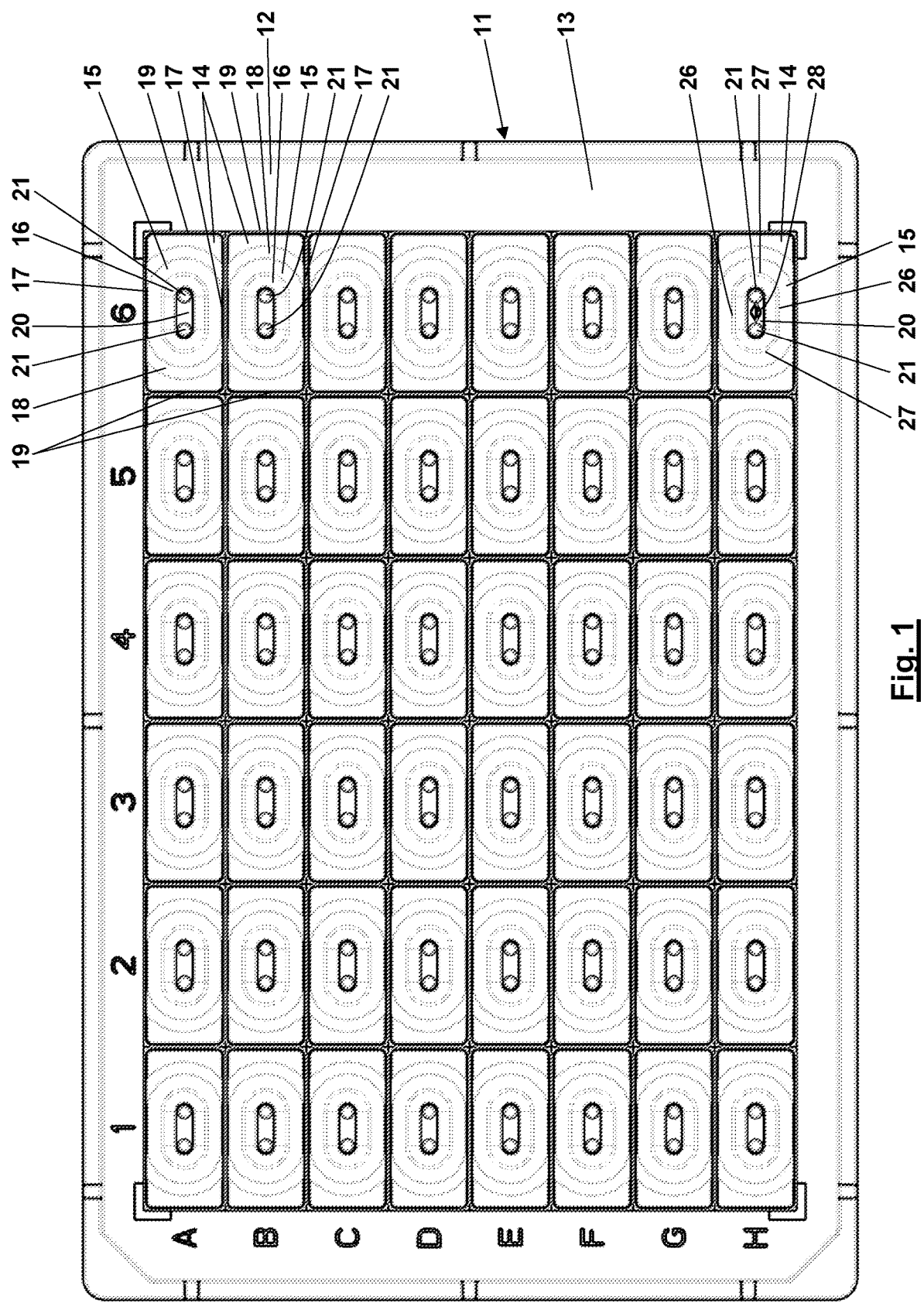
FIG. 1 shows a well plate according to the invention comprising a plurality of cavities in an upper side in a view from above.

The invention particularly relates to a well plate and a method of use of such a well plate for the manufacture and investigation of rings of artificial myocardial muscle and skeletal muscle tissue.

Generally, however, the well plate and the method of its use may also be employed for producing and investigating rings of other cells and cell mixtures, like for example of cells of connective tissue or organ cell like, for example, neurons, hepatocytes, or of other substance like, for example, electro- or magneto-rheological polymers.

In the entire present description and the appending claims, the term "well plate" is not to be understood as a limitation. Thus, generally, the term for example also covers culture dishes with at least one cavity as soon as the at least one cavity has the features which are defined for the at least one cavity of the well plate here.

In a well plate according to the invention comprising a plate main body and at least one cavity in an upper side of the plate main body, wherein an upwardly open annular channel is formed in the at least one cavity, the annular channel being delimited at an inner circumference thereof by a closed circumferential wall, a horizontal outer circumference of the circumferential wall decreases from bottom to top up to an upper edge of the circumferential wall, and within the horizontal outer circumference of the circumferential wall, at its upper edge, at least two retaining elements upwardly connect to the upper edge of the circumferential wall. Here, the at least two retaining elements are at a free horizontal distance from one another, and at least one of the at least two retaining elements is elastically supported at the plate main body in horizontal direction.

The term annular channel is to be understood here such that it does not require a particular shape, particularly no circular shape of the channel designated in this way or of the closed circumferential wall delimiting it at the inner circumference thereof. Instead, this term covers each continuous and closed loop channel. The cross-section of the annular channel may be constant over its inner circumference. This, however, is not compulsory.

If a suspension of connective tissue cells, like for example fibroblasts, and of further cells, like for example myocardial muscle cells, is placed in the annular channel in the at least one cavity of the well plate according to the invention, the suspension optionally also comprising a hydrogel, and a ring being formed out of the suspension which abuts against the circumferential wall, this ring automatically moves upwards due to the outer circumference of the ring decreasing in upward direction. The velocity of this upward movement of the ring depends on the tension of the ring at which it abuts against the circumferential wall, on the derivative of the horizontal circumference of the wall with respect to the height above the bottom of the annular channel, and on the static friction between the ring and the circumferential wall. The upward movement of the ring continues until the ring passes the upper edge of the wall and progresses onto the retaining elements upwardly connecting to the wall. These at least two retaining elements receive the ring. Due to the fact that at least one of them is elastically supported at the plate body in horizontal direction, they are elastically supported at each other and thus fulfill the function of stretchers for the ring. Thus, when using the well plate according to the invention, there is no necessity of removing a ring made in the annular channel and abutting against the circumferential wall forming the inner circumference of the annular channel from the wall and of transferring it onto stretchers. Instead, this transfer occurs automatically with the contraction of the ring because of the horizontal circumference of the circumferential wall decreasing upwardly. For this purpose, the horizontal circumference of the circumferential wall does not need to decrease upwardly in a continuous or even in a strictly monotonic way, although this is preferred.

In the well plate, the retaining elements may generally be supported at a further body which is movable with regard to the base body of the well plate. Preferably, however, each of the at least two retaining elements is supported at the plate main body within the at least one cavity. As a result, the well plate has an overall simple construction. Its use is also made easier, because a ring produced in a cavity of the well plate does not need to be taken out of the cavity for its investigation. Instead, is intended to investigate the respective ring in the same cavity on the retaining elements above the upper edge of the circumferential wall.

Thus, in this embodiment of the well plate according to the invention, at least the retaining element elastically supported at the plate body is part of such a retaining finger. Due to the retaining finger, the respective retaining element is soft-elastically supported in a simple way. This both applies if the respective retaining finger is elastically deformable as such and if the retaining finger is stiff but elastically supported. In both cases, the softness of the support of the respective retaining element increases with the length of the retaining finger between the retaining element and its connection to the plate main body.

In order to provide for a simple connection of the respective retaining finger to the plate main body and nevertheless realize a certain length between the retaining element and the connection, the circumferential wall may enclose at least an upper section of an upwardly open blind hole, at the bottom of which the retaining finger is supported at the plate main body. Then, the length of the blind hole corresponds to the length of the retaining finger between the retaining element and its connection to the plate main body. The blind hole is open at the top where the retaining finger emerges, and it is part of the cavity but not part of the annular channel.

The respective retaining finger may, for example, be positively substance-jointed, i.e. chemically-jointed to the bottom of the blind hole. This, however, requires a direct formation of the retaining finger at or a problematic gluing of the retaining finger to the plate main body at the bottom of the blind hole.

In an embodiment of the well plate, the or each retaining finger is made as one part together with a base plate which is force fitted at the bottom of the blind hole. For this purpose, the blind hole may conically taper downwards, and the base plate may be made of elastic material at a slight oversize and be pressed into the blind hole. For a friction lock of the base plate at the bottom of the blind hole, any suitable material combination with a high surface tension for aqueous liquids getting into the blind hole may already be sufficient. As long as the desired elastic support of the retaining element is achieved, the blind hole may be filled to a larger extent or even completely with the base plate or with any other mounting body for the retaining fingers.

As already indicated, the or each retaining finger may be bending elastic. This does not exclude that it is additionally made together with the above mentioned base plate of a bending elastic material and also elastically mounted to the plate main body. Alternatively, only the base plate may be made of a bending elastic material to achieve a bending elasticity of the or each retaining finger, without the material of the or each retaining finger being bending elastic itself.

All elasticities occurring, which have an influence on the elastic support of the at least two retaining elements at one another, may be adjusted to one another such that a horizontal force of 1 mN between the at least two retaining elements at the two associated retaining fingers results in a relative horizontal deviation of free ends of the two retaining fingers by 1 to 50% of a resting distance of the unloaded retaining fingers or—like for example in case of a well plate for producing and investigating rings of artificial myocardial muscle tissue—of 10 to 30%. Simultaneously or alternatively, the horizontal force of 1 mN between the at least two retaining elements at the two associated retaining fingers may result in a relative horizontal deviation of the free ends of the two retaining fingers in a range of 20 to 1,000 µm or of 50 to 500 µm. It is to be understood that the deviation does not reach an arbitrary value in the range mentioned but increases with the force, and with the horizontal force of 1 mN reaches that value which is defined by the elasticity of the retaining fingers and their connection.

The elasticity of the retaining fingers necessary for this purpose may, for example, be achieved in that the or each retaining finger has a diameter of 0.5 to 3 mm or more particular of 0.75 to 2 mm and/or that the or each retaining finger has a length of 5 to 10 mm from the bottom of the blind hole up to the retaining element formed at it and/or an overall length of 10 to 20 mm. The overall length of the retaining fingers does play a non-irrelevant role insofar as that the relative deviation of the retaining fingers in the area of the retaining elements formed thereat can be increased by a pointer area upwardly extending beyond the retaining element. A force of x mN which alters the distance of the retaining elements by y µm may for example alter the distance of free upper ends of the pointer areas by 2y µm and thus be more easily registered between the free upper ends of the pointer areas. Further, the or each retaining finger may extend beyond a culture medium filled into the cavity due to is overall length so that its orientation may be optically registered particularly easily.

Particularly, such a material having a modulus of elasticity in a range from 0.5 to 50 MPa or more particular of 1 to 10 MPa, i.e. of about 5 MPa may be used as a material for forming the or each elastic retaining finger. It also applies here that the area mentioned is no tolerance area but that the material, within this area, has an as constant modulus of elasticity as possible.

Even if the or each retaining finger, with its free end, extends beyond the retaining element formed at it, it preferably ends below the upper side of the plate main body. In this way, a danger of damages to the retaining fingers, for example by stacking well plates according to the invention or otherwise handling the well plates according to the invention, is reduced.

Preferably, the or each retaining finger is made of a material optically contrastive with regard to the plate main body. This, for example, means that the plate main body is made of a white, another bright or transparent material, whereas the or each retaining finger is made of a black or dark and/or non-transparent material. Then, the retaining finger, as a rule, also contrasts well with regard to a culture medium placed in the cavity. The or each retaining finger may alternatively or additionally also be made of a material which in contrast to the plate main body is fluorescent to provide the optical contrast by illumination with excitation light for the fluorescent material.

In an embodiment of the well plate, at least two of the retaining elements are formed at retaining fingers which each at least comprise an electrically conductive partial area extending up into the retaining element, wherein the electrically conductive partial area of the at least two retaining fingers can be electrically contacted from the bottom side of the plate main body. By making use of this electric contactability, rings abutting against the retaining elements may be electrically excited or stimulated. This both applies to rings of artificial muscle tissue like myocardial muscle or skeletal muscle tissue and to rings of artificial neural tissue and rings of electro-rheological material.

In another embodiment of the well plate, one of the retaining elements is electrically conductive at at least one point of contact with the tissue to form one electrode. This retaining element may be, but does not need to be, the at least one retaining element elastically supported at the plate main body. A counter electrode is provided at another position in the cavity such that it contacts the filled-in culture medium. The electrode formed at the retaining element and the counter electrode may be electrically contactable from outside the cavity.

For forming the respective retaining element, the or each retaining finger may comprise a horizontal notch that connects to the circumferential wall delimiting the annular channel at its inner circumference, or a bulge at a slightly higher position. By this notch or bulge, the respective ring is held in place when it separates from the circumferential wall. However, it turns out that such a notch or bulge for forming a geometrically defined retaining element is not essential. The respective ring keeps its place on each retaining finger directly above the upper edge of the circumferential wall after separation from the circumferential wall even if the retaining fingers run through upwards with a smooth surface.

The horizontal outer circumference of the circumferential wall may particularly be made up of two straight sections which are parallel to each other, and two semicircular arches which connect the ends of the two straight sections. This results into a ring which is extended in parallel to the straight sections and which is adapted to being stretched between two retaining elements which are correspondingly to be arranged above the semicircular arches of the horizontal outer circumference above the upper edge of the circumferential wall.

In this embodiment of the well plate, both the distance of the straight sections and a radius of the semicircular arches may decrease from bottom to top such that the wall has an angle of inclination with regard to the vertical direction everywhere. This angle of inclination may be between 15° to 65° or more particular between 35° and 55°, i.e. about 45°. This angle of inclination does not needs to be the same over the entire outer circumference of the circumferential wall. For example, the angle of inclination may be higher in the area of the straight sections than in the area of the circumferential arches, because the tension of the ring formed and thus the force directed upwards due to the inclination of the wall may be higher there.

The annular channel may be delimited at its outer circumference by a circumferential wall which, in at least one section, has an angle of inclination with regard to the vertical direction of 15 to 65° or more particular of 35 to 50°, i.e. of about 45°, outwardly. In this way, an inflow surface for softly letting a suspension flow into the annular channel is formed. The annular channel may have a volume of 50 to 1,500 µl or more particular of 100 to 250 µl. This dimensioning of the annular channel is well suited for making rings of an inner circumference of 6 to 20 mm.

For an electrical stimulation the material of the ring by an electric field, two electrode free spaces may be formed at the outer circumference of the at least one cavity in direction of the horizontal distance of the at least two retaining elements. Here, the electrodes which are typically no part of the well plate as such may be immersed into the cavity from above. For stimulating the material of the ring by a magnetic field, the entire well plate may be arranged within one or between two toroids.

As a rule, a bottom of the annular channel and the upper edge of the circumferential wall run horizontally in the well plate, and the at least one cavity is closed except of its opening at the upper side of the plate body.

If the well plate shall be used for producing and investigating artificial tissue, the at least one cavity has to be completely lined with biocompatible material, for the purpose of which the plate base body and the retaining fingers attached thereto may completely be made of a biocompatible material. Even if no rings of biological material are formed, it is preferred that the circumferential wall, which delimits the annular channel at its inner circumference, is made of a hydrophobic material. Further, it is preferred that this material is smooth, i.e. has a low surface roughness. Thus, the static friction between the circumferential wall and the ring is reduced.

For producing a plurality of rings and extensive investigations, the well plate may be provided with a plurality of cavities in two horizontal directions which are orthogonal to each other.

In a use of the well plate, a suspension of connective tissue cells and further cells will be placed in the annular channel. The cavity is filled up with a culture medium up to beyond the upper edge of the circumferential wall and preferably up to above the retaining elements. With maturing of the tissue its tension increases, and it climbs up the circumferential wall until it is held by the retaining elements. Contractions of the ring occurring then, which are spontaneous with myocardial muscle tissue and which may be induced by example electrical stimulation with skeletal muscle tissue are monitored with a camera based on movements of a free upper end of the at least one elastically supported retaining element or each retaining element or a pointer area upwardly connecting thereto.

The suspension may particularly be an aqueous suspension of a hydrogel and of muscle cells, particularly of myocardial muscle or skeletal muscle cells.

The further cells may also be hepatocytes or neurons, i.e. neuronal cells.

Filling up the cavity with the culture medium may take place after a predetermined waiting time which is selected such that, upon addition of the culture medium, a flushing out of components of the hydrogel is avoided.

The cavity may be filled with the culture medium beyond the retaining elements, wherein a free upper end of the or each retaining finger may extend beyond the culture medium to make it easier to register movements of the free upper ends of the or each retaining finger with a camera. Generally, the culture medium may also cover the free ends which are monitored with the camera.

Not only for electrically exciting artificial skeletal muscle tissue, but also electrically exciting artificial myocardial muscle tissue or electrorheological material, an electric voltage of varying amplitude, like for example in form of individual voltage pulses or in form of a unipolar or bipolar square wave voltage may be applied between the conductive partial areas of the retaining fingers or between electrodes at the electrode free spaces of the well plate, whereas the movements of the free upper ends of the or each retaining finger are registered with the camera. Particularly, the registered movement may be correlated with the composition of the suspension and/or the frequency and/or the amplitude of the electric voltage and/or the composition and temperature of the culture medium and/or substances added to the culture medium or the like. For example, different pharmacologically or toxicologically active substances or components may be added, and it may then be checked with which active substances or active components or at which concentrations of the active substances or active components a quantifiable effect on, for example, the contractility with regard to the deflection, spontaneous beating frequency, basic tension, speed of contraction and/or relaxation is recognizable.

The electric excitation of the artificial tissue may also take place without monitoring with the camera to, for example, enhance the maturing or purposefully influence the maturing of the tissue.

If the culture medium placed into the cavity is colored, the culture medium is preferably adjusted color-wise with regard to the or each retaining finger such that the or each retaining finger is optically contrastive with regard to the culture medium. For example, the culture medium may be colored due to a pH-indicator. It is to be understood that the color-wise adjustment of the culture medium with regard to the or each retaining finger implies that, for a culture media of a certain color, the or each retaining finger may be provided in a color contrastive thereto.

Now referring in greater detail to the drawings, a well plate 11 depicted in FIG. 1 comprises a plate main body 12 which features a generally plane upper side 3 of the well plate 11. A plurality of cavities 14 is formed in the upper side 3, which each have rectangular horizontal overall dimensions. The cavities 14 are arranged in eight lines A to H and six columns 1 to 6. An annular channel 15 is formed at the bottom of each cavity 14, which is delimited at an inner circumference thereof by a circumferential wall 16. At its outer circumference, the annular channel 15 is continuously delimited, in sections by longitudinal walls 17, which delimit the respective cavity at its longitudinal sides, and in sections by walls 18, which upwardly turn into cross walls 19 which delimit the respective cavity 14 at its small sides. Within the continuous wall 16, a blind hole 20 is formed in each cavity 14 out of which two retaining fingers 21 extend upwardly. The horizontal outer circumference of the circumferential wall—and in a similar way also the annular channel 15 at the bottom of each cavity—is assembled of two straight sections 16 which are parallel with regard to each other, and two semicircular arches 27 connecting the free ends of the straight sections 26. In horizontal directions, the blind hole 20 is extended in the longitudinal direction of the respective cavity 14 and extends over the straight sections up into the semicircular arches. The retaining fingers 21 at the two ends of the longitudinally extended blind hole 20 are essentially oriented vertically, and they are arranged at a free horizontal distance 28 with regard to each other.

Figure 2:
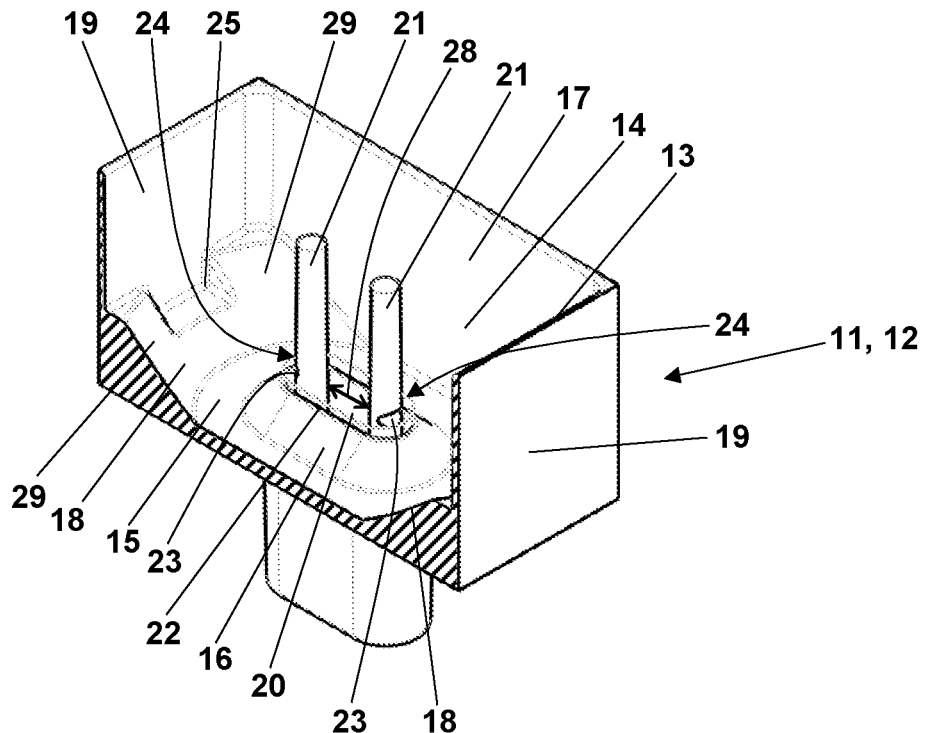
FIG. 2 is a perspective view of one of the cavities of the well plate according to FIG. 1.

FIG. 2 shows one of the cavities 14 of the well plate 11 in a perspective view, wherein one of its longitudinal walls 17 is removed to give a free view into the interior of the cavity 14. Thus, it can be seen that, above an upper edge 22 of the circumferential wall 16, notches 23 are provided in the retaining fingers 21 to form retaining elements 24. Further, at the small sides of the cavities 14, in front of the walls 19, electrode free spaces 25 are left free at the height of the retaining elements 24. FIG. 2 makes clear that the horizontal outer circumference of the circumferential wall 16 decreases from bottom to top and that the retaining elements 24 adjoin the upper edge 22 of the circumferential wall 16 in such a way that they continue the circumferential wall 16 in upward direction except of the free distance 28 of the retaining fingers. Next to the electrode free spaces, the outer walls 18 of the annular channel 15 inclined outwardly rise locally and thus form inflow surfaces 29 over which the annular channel 15 may be filled in a controlled way.

Figure 3:
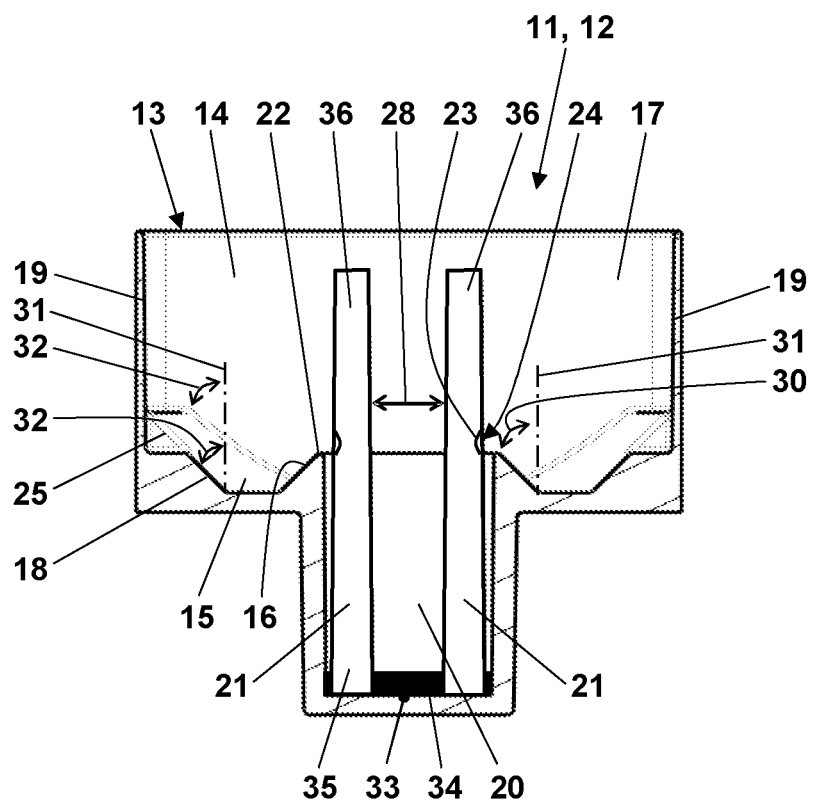
FIG. 3 shows a vertical longitudinal section through the cavity according to FIG. 2.
Figure 4:
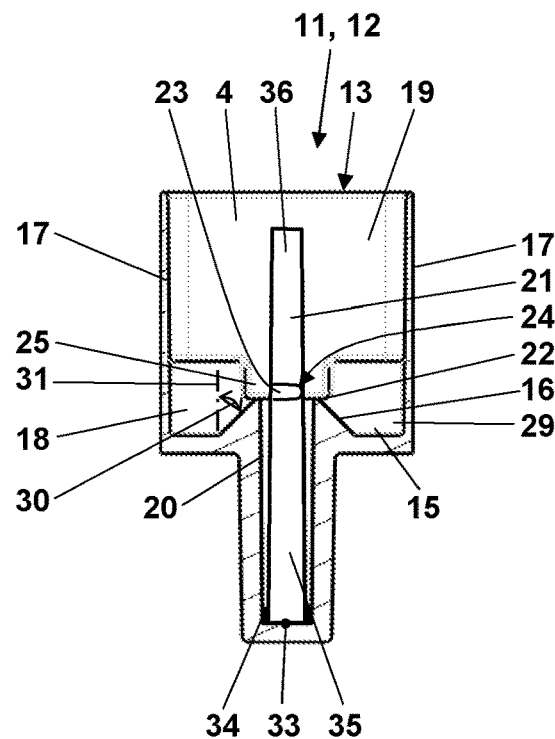
FIG. 4 shows a vertical section through the cavity according to FIG. 2.

In the longitudinal section according to FIG. 3 and the cross-section according to FIG. 4, an angle of inclination 30 of the circumferential wall 16 with regard to the vertical direction 31 is highlighted, which is here 45° everywhere but which may generally also be smaller or greater. An angle of inclination 32 of the wall 18 with regard to the vertical direction 31 is also about 45° here, but it may also be smaller or greater. The fixation of the retaining fingers 21 at the bottom 33 of the blind hole 20 is effected via a base plate 34 which is made of an elastic material 35 as one part together with the retaining fingers 21. The base plate 34 may be inserted into the blind hole 20 in a force fitting way. Often, surface tensions well-adjusted to each other are sufficient to hold the base plate 34 at the bottom 33 of the blind hole 20 and, thus, to achieve a defined basic orientation of the retaining fingers 21 in the cavity 14. The retaining fingers 21 may slightly taper upwardly to be easily demolded out of a mold. Correspondingly, the free cross-section of the cavity 14 may slightly increase upwardly at all places, like within the blind hole 20 to make demolding of the plate main body 12 out of a mold easier. The retaining fingers, with pointer areas 36, extend upwardly beyond the retaining elements formed thereon but end below the upper side 13 of the plate main body 12.

Figure 5:
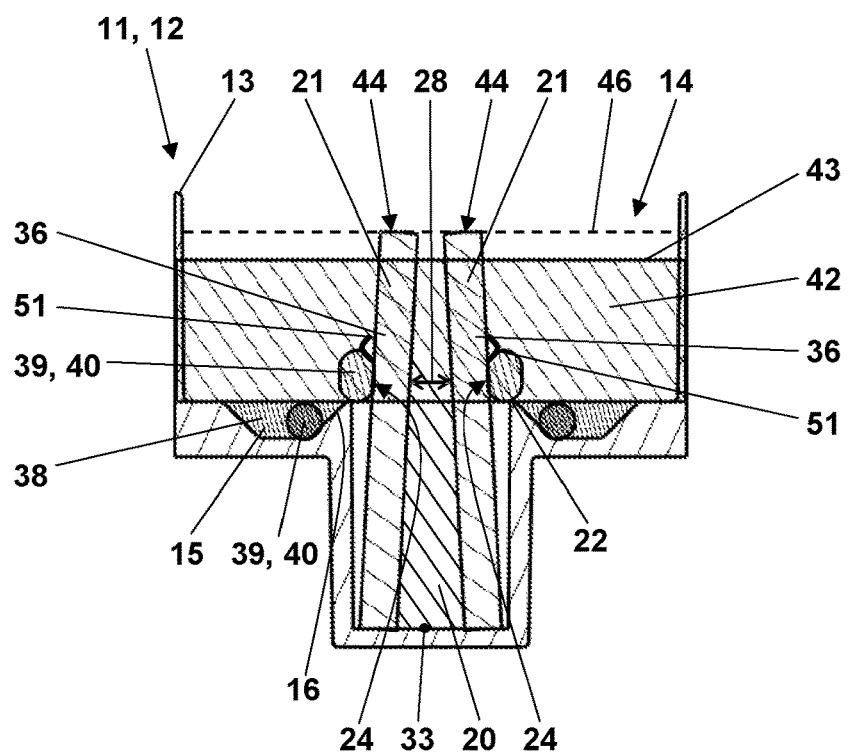
FIG. 5 shows a vertical longitudinal section through a slightly different embodiment of the cavity according to FIG. 2 in a use according to the invention of the well plate according to the invention.
Figure 6:
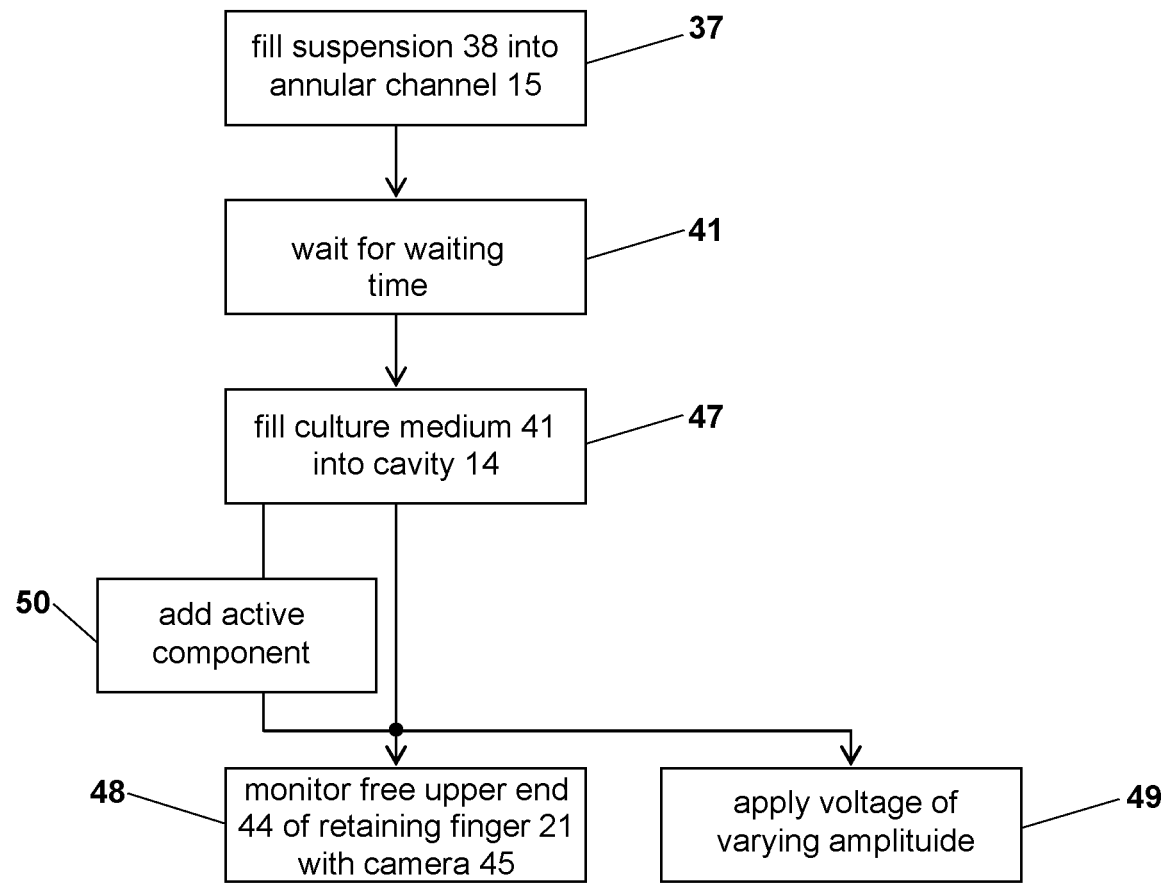
FIG. 6 is a block diagram of the method according to the invention.

FIG. 5, by means of a cavity 14, and FIG. 6, by means of a block diagram, illustrate the use according to the invention of the well plate 11 according to the invention. In a first step 37, the annular channel 15 is filled with a suspension 38, for example of a hydrogel and of myocardial muscle cells in an aqueous solution. In a step 41, the hydrogel solidifies with the myocardial cells within a waiting time of ideally 30 min up to a few hours. Then, in a step 47, the cavity 14 may be filled with a culture medium 42 up to a level 43. In the culture medium 42, a ring 39 of artificial myocardial muscle tissue is typically formed within 24 to 72 h. The ring 39 contracts and thus moves up the circumferential wall 16. The level 43 of the culture medium is selected such that the ring 39 completely stays within the culture medium, if it ascends beyond the upper edge 22 of the circumferential wall 16 and then abuts against the retaining elements 24 at the retaining fingers 21. At their upper ends, the retaining elements 24 comprise horizontal bulges of the retaining fingers 21. Via the retaining fingers 21 they are elastically supported at each other and thus act as stretchers for the ring abutting against them. When making the ring 39 from artificial myocardial muscle tissue, the ring 39 automatically starts with periodic contractions. In a step 49, the frequency of these contractions may be determined by an external electrical field or direct electrical stimulation of the ring 39 with an electric voltage of varying amplitude, like for example in form of individual voltage pulses or in form of an unipolar or bipolar square wave voltage. When making the ring 39, for example, from artificial skeletal muscle tissue or also from electrorheological material, the contractions are only induced by electric fields or directly applied electric voltages.

The contractions may in any case be registered in a step 48 by monitoring the free ends 44 by means of a camera 45 whose focal plane 46 is arranged such that the camera 45 exactly images the free ends 44 sharply. Thus, changes of the free distances 28 are quantitatively registered with the camera 45 with regard to time, course and extend. Suitable optical conditions for monitoring the movement of the free ends 44 by means of the camera 45 are provided in that the level 43 of the culture medium 42 is below the free ends 44 of the pointer areas 46 of the retaining fingers 21. The free ends 44 extending out of the culture medium 42 result in a higher contrast in the images of the camera than when covered with the culture medium 42 which would, however, generally also be possible in the use according to the invention of the well plate 11 according to the invention.

FIG. 6 illustrates that the step 49 of applying the electrical voltage occurs simultaneously with the step 48 of monitoring the retaining fingers 21 with the camera 45. During or after the step 47 of adding the culture medium 42 in the cavity 14, a further optional step 50 may occur in which an active component is added to the culture medium. This step 50 may occur prior to or during the steps 48 and 49, wherein the step 49 is optional. Thus, the effects of this active component on the artificial myocardial muscle tissue 40 may be investigated, for example with regard to how the contractility, measured as the dynamic variation of the free distance 28 of the retaining fingers 21, varies.

In FIG. 5 the two retaining fingers 21 are not connected via a base plate but individually positively substance-jointed at the bottom 33 of the blind hole 20. This may, for example, be accomplished during printing the well plate in a 3D-printer and/or by gluing or fusing the retaining fingers to the well plate.

Many variations and modifications may be made to the preferred embodiments of the invention without departing substantially from the spirit and principles of the invention. All such modifications and variations are intended to be included herein within the scope of the present invention, as defined by the following claims.

We claim:

1. A well plate comprising
a plate main body,
at least one cavity in an upper side of the plate main body,
an upwardly open annular channel being formed in the at least one cavity,
a closed circumferential wall delimiting the annular channel at an inner circumference thereof,
  wherein a horizontal outer circumference of the circumferential wall decreases from bottom to top up to an upper edge of the circumferential wall, and
at least two retaining elements connecting upwardly to the upper edge of the circumferential wall, within the horizontal circumference of the circumferential wall at its upper edge,
  wherein the at least two retaining elements are at a free horizontal distance (28) to one another, and
  wherein at least one of the at least two retaining elements is elastically supported at the plate main body in horizontal direction.

2. The well plate of claim 1, wherein each of the at least two retaining elements is supported at the plate main body in the at least one cavity.

3. The well plate of claim 1, wherein each of the at least two retaining elements is a part of one of at least two retaining fingers extending in vertical direction.

4. The well plate of claim 3, wherein the circumferential wall encloses at least an upper section of an upwardly open blind hole, the at least two retaining fingers being supported at the plate main body at the bottom of the upwardly open blind hole.

5. The well plate of claim 4, wherein the at least two retaining fingers are made in one part with a base plate which is force fitted at the bottom of the blind hole.

6. The well plate of claim 3, wherein the at least two retaining fingers are bending elastic.

7. The well plate of claim 3, wherein the at least two retaining elements provided at the at least two retaining fingers are elastically supported at one another in such a way that a horizontal force of 1 mN between the at least two retaining elements results in a relative horizontal deflection of free ends of the at least two retaining fingers which is at least in one of a range from 50 to 500 μm and a range from 10 to 30% of a resting distance of the at least two retaining fingers.

8. The well plate of claim 3, wherein each of the at least two retaining fingers has at least one of
a diameter of 0.75 to 2.0 mm,
a length from the bottom of the blind hole up to the retaining element formed at the holding finger of 5 to 10 mm, and
an overall length from the bottom of the blind hole up to its free end of 10 to 20 mm.

9. The well plate of claim 3, wherein each of the at least two retaining fingers extends upwardly beyond the retaining element with a pointer area.

10. The well plate of claim 3, wherein each of the at least two retaining fingers is made of a material having a modulus of elasticity in a range from 1 to 10 MPa.

11. The well plate of claim 3, wherein each of the at least two retaining fingers ends below the upper side of the plate main body.

12. The well plate of claim 3, wherein each of the at least two retaining fingers is made of a material which is selected from materials optically contrastive with regard to the plate main body and fluorescent materials.

13. The well plate of claim 3, wherein each of the at least two retaining fingers comprises at least one electrically conductive partial area extending up into the respective one of the at least two retaining elements, the electrically conductive partial areas of the at least two retaining fingers being electrically contactable from the bottom side of the plate main body.

14. The well plate of claim 3, wherein each of the at least two retaining fingers has a horizontal notch or bulge in an area of the respective one of the at least two retaining elements.

15. The well plate of claim 1, wherein the horizontal outer circumference of the circumferential wall is made up of two straight sections which are parallel to each other and two semicircular arches connecting the ends of the two straight sections.

16. The well plate of claim 1, wherein at least one of a lateral distance of the two straight sections and a radius of the semicircular arches decreases from bottom to top.

17. The well plate of claim 1, wherein an angle of inclination of the circumferential wall with regard to vertical direction is in a range from 35° to 55°.

18. The well plate of claim 1, wherein the annular channel at an outer circumference thereof is delimited by walls which at least partially comprise an outward inclination angle with regard to vertical direction in a range from 35° to 55°.

19. The well plate of claim 1, wherein the annular channel has a volume in a range from 100 to 250 μl.

20. The well plate of claim 1, wherein, in a direction of the horizontal distance of the at least two retaining elements, two electrode free spaces are formed an the outer circumference of the at least one cavity.

21. The well plate of claim 1, wherein a bottom of the annular channel and the upper edge of the circumferential wall extend horizontally, and wherein the at least one cavity is closed except of its opening at the upper side of the plate main body.

22. The well plate of claim 1, wherein the at least one cavity is completely lined with biocompatible materials.

23. The well plate of claim 1, wherein the circumferential wall is made of a material selected form smooth and hydrophobic materials.

24. The well plate of claim 1, wherein a plurality of cavities in the upper side of the plate main body are arranged side-by-side in two horizontal directions.

25. A method of use of a well plate claim 3, comprising
placing a suspension of connective tissue cells and further cells into the annular channel,
filling the cavity with a culture medium up to above the at least two retaining elements, and
monitoring movements of at least one free upper end of at least one of the at least two retaining fingers with a camera.

26. The method of claim 25, wherein the cavity is filled with the culture medium up to such a level that the at least one free upper end extends beyond the culture medium.

27. The method of claim 25, wherein the further cells are selected from muscle cells, heart muscle cells or skeletal muscle cells.

28. The method of claim 25, wherein the suspension further includes a hydrogel.

29. The method of claim 25, wherein an electric voltage of varying amplitude is applied between at least two electrodes, each of the at least two electrodes being located at one of the at least two retaining elements or in the culture medium.

30. The method of claim 25, wherein the culture medium is adapted to the at least one upper end of the at least one of the at least two retaining fingers in terms of color such that the at least one upper end is optically contrastive with regard to the culture medium.

* * * * *